United States Patent [19]

Goertz et al.

[11] Patent Number: 4,841,066
[45] Date of Patent: Jun. 20, 1989

[54] PREPARATION OF 3-METHYL-1-VINYLIMIDAZOLIUM CHLORIDES

[75] Inventors: Hans-Helmut Goertz, Freinsheim; Ferdinand Straub, Hockenheim; Axel Sanner, Frankenthal; Albrecht Kolb, Weisenheim; Hans-Juergen Raubenheimer, Ketsch; Friedrich Vogel, Wachenheim, all of Fed. Rep. of Germany

[73] Assignee: BASF Aktiengesellschaft, Ludwigshafen, Fed. Rep. of Germany

[21] Appl. No.: 49,314

[22] Filed: May 13, 1987

[30] Foreign Application Priority Data

May 21, 1986 [DE] Fed. Rep. of Germany ....... 3617069

[51] Int. Cl.$^4$ .......................................... C07D 233/58
[52] U.S. Cl. ..................................................... 548/335
[58] Field of Search .......................................... 548/335

[56] References Cited

U.S. PATENT DOCUMENTS 3,948,866  4/1976  Pennewiss et al. ............. 526/312 X
4,692,317  9/1987  Greaves ........................... 422/16 X

FOREIGN PATENT DOCUMENTS 626475  7/1949  United Kingdom ............... 548/335

OTHER PUBLICATIONS

Strettwieser, A., et al., *Introduction To Organic Chemistry*, 3rd Ed., MacMillan, N.Y. 1985, p. 172.
Gregor M., et al., *J. Phys. Chem.* 61 (1957), pp. 1347–1352.
Salamone, J., et al., American Chemical Society, Polymer Preprints, 15, (1974), pp. 462–467.
Salamone, J., et al., American Chemical Society, Polymer Preprints, 13, (1972), pp. 271–272.
Shostakovskii, M., et al., *Khim. Geterotsiklich. Soed.* 7 (1971), pp. 958–960.

*Primary Examiner*—Richard A. Schwartz
*Attorney, Agent, or Firm*—Oblon, Fisher, Spivak, McClelland & Maier

[57] ABSTRACT

3-Methyl-1-vinylimidazolium chlorides are prepared by quaternizing N-vinylimidazoles in aqueous solution with methyl chloride and are used for the preparation of water-soluble homo- or copolymers.

4 Claims, No Drawings

PREPARATION OF 3-METHYL-1-VINYLIMIDAZOLIUM CHLORIDES

The present invention relates to the preparation of 3-methyl-1-vinylimidazolium chlorides by quaternization of N-vinylimidazoles in aqueous solution with methyl chloride, and their use for the preparation of water-soluble homo- or copolymers.

Water-soluble cationic polymers containing 3-methyl-1-vinylimidazolium chlorides as monomeric structural elements can be prepared in principle by two methods:

The corresponding N-vinylimidazole is homopolymerized or copolymerized, and the resulting polymer is then quaternized with a methylating reagent. This method is described in, for example, J. Phys. Chem. 61 (1957), 1347–1352, polyvinylimidazole dissolved in methanol being reacted with methyl iodide.

It is also possible for the quaternization to be carried out at the monomer stage, and the resulting quaternary monomer to be used in the polymerization. Examples of this method too are known from the literature. For example, J. C. Salamone et al., in a series of papers, ACS Polymer Preprints 15 (1974), 462–467 and 13 (1972), 271–272, describe the reaction of N-vinylimidazoles with methyl iodide or dimethyl sulfate to give quaternary ammonium salts. The procedure they adopt comprises reacting the monomers, eg. N-vinylimidazole, in ethyl acetate as the solvent, with the alkylating agent and isolating the resulting salts as solids. For the polymerization, the salts are redissolved together with suitable monomers.

The quaternization of N-vinylimidazole with dimethyl sulfate or methyl iodide is a conventional procedure and is frequently described in the literature. On the other hand, the use of methyl chloride as a methylating or quaternization reagent is unusual, although the methochlorides obtained have the advantage of a lower molecular weight and hence a higher charge density. Khim. Geterotsiklich. Soed. 7 (1971), 958–960 describes the quaternization of vinylimidazole with alkyl iodides, eg. methyl iodide, and alkyl bromides without the addition of a solvent and concludes that vinylimidazole does not react with alkyl chlorides, although British Pat. No. 626,475 discloses that, for example, 1-n-decyl-2-methylimidazole can react with methyl chloride in a closed vessel.

It is generally known that polar solvents, such as nitromethane, acetonitrile or alcohols, are particularly useful as solvents for quaternization reactions with alkyl halides. On the other hand, because the alkyl halides exhibit little or no solubility in water, the latter appears less suitable, as indicated in, for example, Houben-Weyl, Methoden der organischen Chemie, Volume XI/2, pages 594–596 (1958). It is also stated there that, owing to the significantly lower activity of the alkyl chlorides, it is advantageous to carry out the alkylation with an alkyl bromide or alkyl iodide and thereafter to effect halogen exchange.

It is an object of the present invention to provide a very simple industrial process for the preparation of 3-methyl-1-vinylimidazolium chlorides by reaction with methyl chloride in aqueous solution.

The present invention relates to a process for the preparation of 3-methyl-1-vinylimidazolium chlorides of the formula I

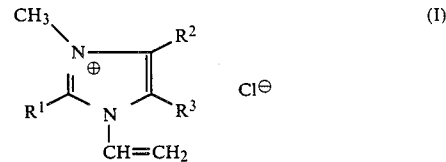

where $R^1$, $R^2$ and $R^3$ are each H or methyl, wherein a 10–70, preferably 25–60, % strength by weight aqueous solution of an N-vinylimidazole of the formula II

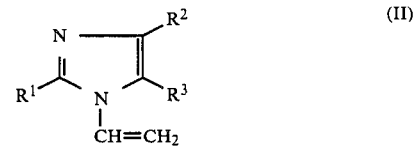

where $R^1$, $R^2$ and $R^3$ are each H or methyl, is reacted with methyl chloride in an amount of 90–110, preferably 94–100, mol % at from 40° to 100° C., preferably from 50° to 90° C., in a closed system.

The preferred starting compounds of the formula II are 1-vinylimidazole and 2-methyl-1-vinylimidazole.

The reaction is carried out in a closed apparatus, the methyl chloride being metered into the heated solution of the quaternized imidazole of the formula II in such a way that the resulting pressure at the stated temperatures during the reaction is from 2 to 15 bar.

Depending in particular on the reaction rate, the temperatures and the apparatus used, methyl chloride is metered at an appropriate rate within the stated pressure range. In apparatuses which are particularly suitable for fairly high pressures and in which good removal of heat is ensured, the reaction can be carried out at higher pressures, within the pressure range described, and with correspondingly faster metering of methyl chloride.

If it is intended to achieve as complete quaternization of the imidazole as possible, at least an equimolar amount or an excess of up to 10 mol % of methyl chloride is added. The preferred amounts of methyl chloride are from 94 to 100, particularly preferably from 94 to 99, mol %. Since the reaction rate noticeably decreases toward the end of the reaction, more complete conversion of the methyl chloride is generally achieved if slightly less than the stoichiometric amount of methyl chloride is used.

In another embodiment, the aqueous solution used can contain a monohydric aliphatic alcohol of 1 to 3 carbon atoms as an additional solvent, advantageously in an amount of 5–30% by weight, based on the water present. Methanol, ethanol, n-propanol and in particular isopropanol are suitable for this purpose.

The quaternization reaction according to the invention is surprising because of the simplicity of the process. It was not foreseeable that, using water as a solvent, it would be possible to achieve complete conversion, since the prior art indicates that a direct reaction is impossible or very difficult and, on the other hand, methyl chloride is only very slightly soluble in water. 1 kg of water dissolves 9 g of methyl chloride at room temperature under 1 bar and only 2.64 g at 60° C., as stated in, for example, Ullmann, Enzyklopädie der Technischen Chemie, Vol. 9, page 405 (1975).

The aqueous solution obtained after the reaction according to the invention can advantageously be used directly for the preparation of correspondingly water-soluble polymers. As a rule, isolation of the resulting 3-methyl-1-vinylimidazolium chloride is therefore unnecessary. The present invention thus also relates to the use of the resulting solutions according to claim 1 for the preparation of water-soluble homo- or copolymers of 1-vinylimidazolium chlorides of the formula I.

Advantageously, the resulting solutions of the 3-methyl-1-vinylimidazolium chlorides are polymerized directly or with other polymerizable monomers in a conventional manner in aqueous or aqueous-alcoholic solutions, using free radical initiators.

Advantageous comonomers are water-soluble unsaturated monomers, for example N-vinylimidazoles of the above formula II, acrylamide and methacrylamide, N-methylolacrylamide and N-methylolmethacrylamide, hydroxyalkyl acrylates and hydroxyalkyl methacrylates where hydroxyalkyl is of 2 to 4 carbon atoms, such as hydroxyethyl (meth)acrylate, hydroxypropyl (meth)acrylate, if necessary in the form of their industrial mixtures, polyethylene glycol (meth)acrylates having from 2 to 50 ethylene oxide units, and in particular N-vinylamides, such as N-vinylpyrrolidone, N-vinylcaprolactam, N-vinylformamide, N-vinylacetamide or N-methyl-N-vinylacetamide.

If necessary, water-insoluble comonomers, such as styrene, α-olefins, such as pentene or butene, alkyl acrylates and methacrylates where alkyl is of 1 to 18 carbon atoms, vinyl carboxylates where the carboxylate radical is of 2 to 10 carbon atoms, such as vinyl acetate or vinyl propionate, can also be copolymerized with the 3-methyl-1-vinylimidazolium chlorides prepared according to the invention. In this process, it is advantageous if an alcohol has already been added to the quaternization mixture in an amount sufficient to produce a homogeneous solution.

The preparation of homopolymers of 1-vinylimidazolium chlorides of the formula I or of water-soluble copolymers of from 97 to 10% by weight of a 3-methyl-1-vinylimidazolium chloride of the formula I and from 3 to 90% by weight of a monomer from the group consisting of N-vinylpyrrolidone, 2-hydroxyethyl acrylate, 2-hydroxyethyl methacrylate and hydroxypropyl acrylate (industrial mixture) is very particularly preferred, the percentages being based on the total weight of the monomers.

The polymerizations are advantageously carried out in 10–50% strength by weight aqueous or aqueous-alcoholic solutions, preferably aqueous isopropanolic solutions, in the presence of a free radical initiator in an amount of from 0.1 to 2.0% by weight, based on the weight of the monomers, at from 40° to 100° C.

Suitable free radical initiators are hydrogen peroxide or inorganic persulfates, as well as organic compounds of the peroxide or azo type. Examples of suitable organic peroxides are dicyclohexyl peroxydicarbonate, dibenzoyl peroxide, dilauroyl peroxide, tert.-butyl perpivalate and tert.-butyl 2-ethylhexanoate, and examples of suitable azo compounds are 2,2′-azobisisobutyrodinitrile, 2,2′-azobis(2,4-dimethylvaleronitrile), 2,2′-azobis(2-amidinopropane) hydrochloride and 4,4′-azobis(4-cyanopentanoic acid).

It is not absolutely essential for the free radical former used to be soluble in water. Water-insoluble initiators can, for example, be dissolved in a lower alcohol of metered in directly without a solvent. The choice of initiator is advantageously determined, inter alia, by the polymerization temperatures, which are preferably from 40° to 100° C.

The molecular weight of the polymers can, if desired, be reduced by adding regulators to the reaction mixture. Examples of suitable regulators are lower alcohols. Where it is advantageous to use them, the lower alcohols are expediently added in the required amount at as early a stage as the preparation of the imidazolium chlorides. Further suitable molecular weight regulators are other compounds conventionally employed for this purpose, for example sulfur compounds, such as 2-mercaptoethanol, butyl mercaptan, dodecyl mercaptan, thioglycollic acid, thioacetic acid or thiolactic acid, halogen compounds, such as carbon tetrachloride or 1,1,1-tribromopropane, and formic acid and their derivatives. By a suitable choice of regulator, initiator, polymerization temperature and monomer concentration, it is possible to establish the K value of the resulting polymer, which is a measure of the molecular weight. The K values of the copolymers obtained are advantageously from 20 to 150, and those of the homopolymers are from 15 to 80, the measurements being carried out on a 1% strength by weight aqueous solution at 25° C.

The polymers obtained have a wide variety of uses, for example as conductive resins, flocculants, hair conditioners, assistants in oil production, etc.

The Examples which follow illustrate the invention. The hydrogenation iodine number is measured in accordance with DIN 53,241 and the K value is measured on a 1% strength by weight solution in water at 25° C. by the Fikentscher method.

EXAMPLE 1

2 kg of 2-methyl-1-vinylimidazole and 1.5 kg of water were heated to 75° C., while stirring, in a 6 L stirred container. The apparatus was closed, after which sufficient chloromethane was metered in to raise the pressure to about 4 bar. The pressure was allowed to drop to about 2 bar, after which further chloromethane was metered in. This procedure was repeated until 450 g (96 mol %, based on 2-methyl-1-vinylimidazole) of chloromethane had been reacted. After cooling, a 58% strength by weight solution of the quaternized monomer was obtained. The hydrogenation iodine number of the solution was 90 (theoretical value 92).

EXAMPLE 2

1 kg of 2-methyl-1-vinylimidazole, 0.21 kg of isopropanol and 0.84 kg of water were introduced into a 6 L stirred container, and the stirred mixture was heated to 75° C. Thereafter, the procedure described in Example 1 was followed until 440 g (94 mol %, based on 3-methyl-1-vinylimidazole) of chloromethane had reacted. The resulting solution had a solids content of 58% and the hydrogenation iodine number was 88 (theoretical value 92).

EXAMPLE 3

1 kg of 1-vinylimidazole and 1.05 kg of water were introduced into a 6 L stirred container, and the stirred mixture was heated to 75° C. Thereafter, the procedure described in Example 1 was followed until 525 g (98 mol %, based on 1-vinylimidazole) of chloromethane had reacted. The resulting solution had a solids content of 59% and a hydrogenation iodine number of 104 (theoretical value 103).

EXAMPLE 4

A solution of 1 kg of 1-vinylimidazole, 0.21 kg of isopropanol and 0.84 kg of water was heated to 73° C., while stirring, in a 6 L stirred container. Thereafter, the procedure described in Example 1 was followed until 520 g (97 mol %, based on vinylimidazole) of chloromethane had reacted. The resulting solution had a solids content of 59% and the hydrogenation iodine number was 104 (theoretical value 103).

Polymerization Examples

EXAMPLE 5

A mixture of 203 g of the monomer solution according to Example 1, 100 g of water and 280 g of vinylpyrrolidone, referred to below as feed 1, was brought to pH 7.5 with concentrated ammonia solution. A second solution, referred to below as feed 2, was prepared from 2 g of 2,2'-azobis-(2-amidinopropane) hydrochloride and 55 g of water.

362 g of water, 50 ml of feed 1 and 5 ml of feed 2 were heated to 75° C., while stirring, in a 2 L glass vessel equipped with a stirrer, a heater, a reflux condenser and metering apparatuses. After the intended temperature had been reached, the remainder of feed 1 was metered in over 4 hours and the remainder of feed 2 over 5 hours at a constant temperature of 75° C. Thereafter, stirring was continued for one hour at this temperature. A clear, highly viscous polymer solution was obtained. The K value of the polymer was 141.5.

EXAMPLE 6

A mixture of 483 g of the monomer solution according to Example 3, 15 g of vinylpyrrolidone and 137 g of water was brought to pH 7.5 with concentrated ammonia solution (feed 1). Feed 2 was prepared from 3 g of 2,2'-azobis-(2-amidinopropane) hydrochloride and 75 g of water.

290 g of water, 100 ml of feed 1 and 8 ml of feed 2 were initially taken in a 2 L glass vessel equipped with a stirrer, a heater, reflux condenser and metering apparatuses, and were heated to 65° C. while stirring. At this temperature, the remainder of feed 1 was metered in over 5 hours and the remainder of feed 2 over 7 hours. Thereafter, stirring was continued for a further hour at this temperature. A clear, viscous polymer solution was obtained. The K value of the polymer was 98.2.

EXAMPLE 7

Feed 1 consisted of a mixture of 855 g of a monomer solution according to Example 4, 275 g of water and 40 g of isopropanol. Feed 2 was prepared from 4.6 g of tert.-butyl 2-ethylhexanoate and 157 g of isopropanol. 40 g of water, 120 ml of feed 1 and 20 ml of feed 2 were initially taken in a 2 L glass vessel equipped with a stirrer, a heater, a reflux condenser and metering apparatuses and were refluxed gently (about 83° C.). Thereafter, the remainder of feed 1 was metered in over 6 hours and the remainder of feed 2 over 8 hours, with constant gentle boiling, after which the mixture was kept at the boil for a further hour. The isopropanol was then expelled by passing in steam. A clear, viscous polymer solution was obtained. The K value of the polymer was 57.8.

EXAMPLE 8

Feed 1 consisted of a mixture of 381 g of a monomer solution according to Example 3, 75 g of 2-hydroxyethyl acrylate and 180 g of water. Feed 2 was prepared from 3 g of 2,2'-azobis-(2-amidinopropane) hydrochloride. 290 g of water, 100 ml of feed 1 and 8 ml of feed 2 were initially taken in a 2 L glass vessel equipped with a stirrer, a heater, a reflux condenser and metering apparatuses and were heated to 65° C. At this temperature, the remainder of feed 1 was metered in over 5 hours and the remainder of feed 2 over 7 hours. Thereafter, stirring was continued for a further hour at this temperature. A cloudy, viscous polymer solution was obtained. The K value of the polymer was 93.

EXAMPLE 9

Feed 1 consisted of a mixture of 203 g of a monomer solution according to Example 3, 280 g of vinylpyrrolidone, 100 g of water and 1.2 g of 2-mercaptoethanol. A solution of 8 g of hydrogen peroxide (30% strength, in 75 g of water) served as feed 2. 320 g of water, 50 ml of feed 1 and 10 ml of feed 2 were initially taken in a 2 L glass vessel equipped with a stirrer, a heater, a reflux condenser and metering apparatuses and were heated to 65° C. At this temperature, the remainder of feed 1 was metered in over 5 hours and the remainder of feed 2 over 7 hours. Stirring was continued for a further hour at this temperature. A clear, viscous polymer solution was obtained. The K value of the polymer was 72.5.

EXAMPLE 10

Feed 1 consisted of 330 g of a monomer solution according to Example 4, 194 g of vinylpyrrolidone and 320 g of water, which was brought to pH 7.5 with concentrated ammonia solution. Feed 2 consisted of a mixture of 2.8 g of tert.-butyl 2-ethylhexanoate in 110 g of isopropanol. 142 g of isopropanol, 88 g of water, 140 ml of feed 1 and 10 ml of feed 2 were initially taken in a glass vessel equipped with a stirrer, a heater, a reflux condenser and metering apparatuses and were boiled gently (at about 83° C.). Thereafter, at this temperature, the remainder of feed 1 was metered in over 8 hours and the remainder of feed 2 over 12 hours. The mixture was then kept at the boil for a further 2 hours, after which the isopropanol was distilled off under atmospheric pressure until the distillation temperature of 100° C. was reached. A clear, viscous polymer solution was obtained. The K value of the polymer was 85.0.

EXAMPLE 11

Feed 1 consisted of a mixture of 381 g of a monomer solution according to Example 3, 75 g of hydroxypropyl acrylate (industrial isomer mixture) and 180 g of water. A solution of 3 g of 2,2'-azobis-(2-amidinopropane) hydrochloride in 75 g of water served as feed 2. 290 g of water, 100 ml of feed 1 and 8 ml of feed 2 were initially taken in a glass vessel equipped with a stirrer, a heater, a reflux condenser and metering apparatuses and were heated to 65° C. At this temperature, the remainder of feed 1 was metered in over 5 hours and the remainder of feed 2 over 7 hours. Stirring was continued for a further hour at 65° C. A slightly cloudy, viscous polymer solution was obtained, this solution becoming clear when diluted to a solids content of 20%. The K value of the polymer was 100.4.

EXAMPLE 12

Feed 1 consisted of a mixture of 203 g of a monomer solution according to Example 3, 100 g of water, 280 g of vinylpyrrolidone and 1.2 g of mercaptoethanol. A solution of 2.4 g of azobis-(2,4-dimethylvaleronitrile) in 75 g of ethanol was used as feed 2. 320 g of water, 50 ml of feed 1 and 7 ml of feed 2 were initially taken in a 2 L glass vessel equipped with a stirrer, a heater, reflux condenser and metering apparatuses and were heated to 65° C. At this temperature, the remainder of feed 1 was metered in over 4 hours and the remainder of feed 2 over 6 hours, after which stirring was continued for a further hour. The ethanol was expelled by passing in steam. A clear, viscous polymer solution was obtained. The K value of the polymer was 78.3.

EXAMPLE 13

Feed 1 consisted of a mixture of 339 g of a monomer solution according to Example 3, 200 g of vinylpyrrolidone, 96 g of water and 1 g of 2-mercaptoethanol, which had been brought to pH 7.5 with concentrated ammonia solution. A solution of 2.4 g of 2,2'-azobis-(2-amidinopropane) hydrochloride in 75 g of water served as feed 2. 196 g of water, 106 ml of feed 1 and 5 ml of feed 2 were initially taken in a 2 L glass vessel equipped with a stirrer, a heater, reflux condenser and metering apparatuses and were heated to 65° C. Thereafter, at this temperature, the remainder of feed 1 was metered in over 5 hours and the remainder of feed 2 over 7 hours, and stirring was continued for a further hour. A clear, viscous polymer solution was obtained. The K value of the polymer was 78.0.

EXAMPLE 14

Feed 1 consisted of a mixture of 203 g of a monomer solution according to Example 3, 100 g of water, 280 g of vinylpyrrolidone and 1.2 g of mercaptoethanol, which had been brought to pH 7.5 with concentrated ammonia solution. 320 g of water, 50 ml of feed 1 and 0.2 g of tert.-butyl perpivalate were initially taken in a 2 L glass vessel equipped with a stirrer, a heater, reflux condenser and metering apparatuses and were heated to 65° C. At this temperature, the remainder of feed 1 was metered in over 4 hours and, at the same time, 0.2 g of tert.-butyl perpivalate was added every 30 minutes, a total of 2.4 g being introduced in the course of 6 hours. Thereafter, stirring was continued for a further hour at this temperature. A clear, viscous polymer solution was obtained. The K value of the polymer was 91.0.

EXAMPLE 15

Feed 1 consisted of a mixture of 203 g of a monomer solution according to Example 1, 125 g of water, 280 g of vinylpyrrolidone and 12 g of potassium formate. To prepare feed 2, 2 g of 4,4'-azobis-(cyanopentanoic acid) were suspended in 50 g of water and brought into solution with about 5 ml of 10% strength sodium hydroxide solution. 338 g of water, 50 ml of feed 1 and 5 ml of feed 2 were initially taken in a glass vessel equipped with a stirrer, a heater, reflux condenser and metering apparatuses and were boiled gently (at about 100° C). At this temperature, the remainder of feed 1 was metered in over 4 hours and the remainder of feed 2 over 5 hours, after which stirring was continued for a further hour at this temperature. A slightly cloudy, viscous polymer solution was obtained. The K value of the polymer was 81.9.

EXAMPLE 16

Feed 1 consisted of a mixture of 381 g of a monomer solution according to Example 3, 75 g of 2-hydroxyethyl methacrylate and 180 g of water. A solution of 3 g of 2,2'-azobis-(2-amidinopropane) hydrochloride in 75 g of water served as feed 2. 290 g of water, 100 ml of feed 1 and 8 ml of feed 2 were initially taken in a glass vessel equipped with a stirrer, heater, reflux condenser and metering apparatuses and were heated to 65° C. At this temperature, the remainder of feed 1 was metered in over 5 hours and the remainder of feed 2 over 7 hours. Stirring was then continued for a further hour at this temperature. A cloudy, viscous polymer solution was obtained, this solution becoming clear when diluted with water to solids contents below 5% by weight. The K value of the polymer was 96.2.

We claim:

1. A process for the preparation of a 3-methyl-l-vinylimidazolium chloride of the formula I

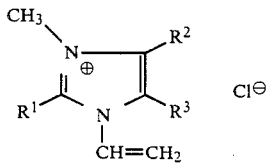

where $R^1$, $R^2$ and $R^3$ are each H or methyl, wherein a 10–70% strength by weight aqueous solution of an N-vinylimidazole of the formula II

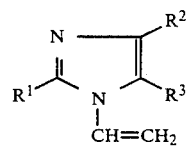

where $R^1$, $R^2$ and $R^3$ are each H or methyl, is reacted with methyl chloride in an amount of from 90 to 110 mol %, based on the N-vinylimidazole of the formula II, at from 40° to 100° C. in a closed system.

2. A process as claimed in claim 1, wherein a 25–60% strength by weight aqueous solution of an N-vinylimidazole of the formula II is reacted with methyl chloride in an amount of from 94 to 100 mol % at from 50° to 90° C.

3. A process as claimed in claim 1, wherein the aqueous solution of the N-vinylimidazole of the formula I additionally contains from 5 to 30% by weight, based on the weight of the water, of a monohydric alcohol of 1 to 3 carbon atoms as a solvent.

4. A process for the preparation of a compound of the formula I as claimed in claim 1, wherein a compound is prepared in which $R^1$ is hydrogen or methyl and $R^2$ and $R^3$ are each hydrogen.

* * * * *